United States Patent
Lefkowitz et al.

(10) Patent No.: US 12,194,102 B2
(45) Date of Patent: Jan. 14, 2025

(54) COMPOSITIONS FOR ENHANCING BIOAVAILABILITY OF PHARMACEUTICALS, SUPPLEMENTS AND INGESTED SUBSTANCES

(71) Applicant: Locus Solutions IPCo, LLC, Solon, OH (US)

(72) Inventors: Andrew R. Lefkowitz, Solon, OH (US); Sean Farmer, Ft. Lauderdale, FL (US); Ken Alibek, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 0 days.

(21) Appl. No.: 18/175,020

(22) Filed: Feb. 27, 2023

(65) Prior Publication Data

US 2023/0201352 A1    Jun. 29, 2023

Related U.S. Application Data

(63) Continuation of application No. 16/632,626, filed as application No. PCT/US2018/042885 on Jul. 19, 2018, now Pat. No. 11,590,231.

(60) Provisional application No. 62/690,365, filed on Jun. 27, 2018, provisional application No. 62/647,974, filed on Mar. 26, 2018, provisional application No. 62/537,502, filed on Jul. 27, 2017.

(51) Int. Cl.
*A61K 47/26* (2006.01)
*A61K 9/51* (2006.01)
*A61K 47/42* (2017.01)

(52) U.S. Cl.
CPC ............ *A61K 47/26* (2013.01); *A61K 9/5123* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 4,902,512 A | 2/1990 | Ishigami et al. |
| 5,756,471 A | 5/1998 | Hillion et al. |
| 5,981,497 A | 11/1999 | Maingault |
| 5,989,583 A | 11/1999 | Amselem |
| 6,596,265 B1 | 7/2003 | Borzeix Concaix |
| 6,759,057 B1 | 7/2004 | Weiner et al. |
| 8,361,779 B2 | 1/2013 | Bergmaier |
| 9,585,903 B2 | 3/2017 | Prabhune et al. |
| 9,931,309 B2 | 4/2018 | Singh et al. |
| 10,065,982 B2 | 9/2018 | Hirata et al. |
| 10,072,208 B2 | 9/2018 | Madduri et al. |
| 10,307,466 B2 | 6/2019 | Suzuki et al. |
| 2002/0123077 A1 | 9/2002 | O'Toole et al. |
| 2003/0228402 A1 | 12/2003 | Franklin et al. |
| 2005/0031549 A1 | 2/2005 | Quay et al. |
| 2010/0267684 A1 | 10/2010 | Seong et al. |
| 2010/0280111 A1* | 11/2010 | Aoki ............... A61K 31/221 514/547 |
| 2011/0044972 A1 | 2/2011 | Fieldhouse et al. |
| 2012/0142621 A1 | 6/2012 | Falus et al. |
| 2012/0302494 A1 | 11/2012 | Guilhabert-Goya et al. |
| 2014/0187507 A1 | 7/2014 | DeFrees et al. |
| 2014/0255420 A1 | 9/2014 | Ilan et al. |
| 2015/0037302 A1 | 2/2015 | Bralkowski et al. |
| 2015/0094273 A1 | 4/2015 | Prabhune et al. |
| 2016/0030322 A1 | 2/2016 | Lu et al. |
| 2016/0073944 A1 | 3/2016 | Lazarini et al. |
| 2016/0083757 A1 | 3/2016 | Fonseca et al. |
| 2016/0309715 A1 | 10/2016 | Diaz de Rienzo et al. |
| 2017/0224636 A1 | 8/2017 | Singh et al. |
| 2017/0340663 A1 | 11/2017 | Cannock |
| 2018/0125980 A1 | 5/2018 | Finley et al. |
| 2019/0054176 A1 | 2/2019 | Touitou |
| 2021/0112787 A1 | 4/2021 | Farmer et al. |

FOREIGN PATENT DOCUMENTS

| | | | |
|---|---|---|---|
| CA | 2223788 | * | 5/1996 |
| CN | 102988981 A | | 3/2013 |
| CN | 103007287 A | | 4/2013 |
| CN | 110769687 A | | 2/2020 |
| EP | 0540074 A1 | | 10/1992 |
| EP | 3117838 A1 | | 1/2017 |
| JP | 2003040767 B2 | | 2/2003 |
| JP | 2006131589 A | | 5/2006 |
| JP | 2009167158 A | | 7/2009 |

(Continued)

OTHER PUBLICATIONS

Kitamoto et al. (Self-assembling properties of glycolipid biosurfactants and their potential application, Current Opinion in colloid and interface science 14 (2009), 315-328). (Year: 2009).*

Adwan, G., et al., "Synergistic Effects of Plant Extracts and Antibiotics on Staphylococcus aureus Strains Isolated from Clinical Specimens." Middle-East Journal of Scientific Research, 2008, 3(3): pp. 134-139.

Bhadoriya, S.S., et al., "Biosurfactants: A New Pharmaceutical Additive for Solubility Enhancement and Pharmaceutical Development." Biochemistry & Pharmacology: Open Access, 2013, 2(2): pp. 1-5.

Coronel-Leon, J., et al., "Optimizing the production of the biosurfactant lichenysin and its application in biofilm control." Journal of Applied Microbiology, 2015, 120: pp. 99-111.

Darne, P.A., et al., "Bioavailability studies of curcumin-sophorolipid nano-conjugates in the aqueous phase: role in the synthesis of uniform gold nanoparticles." RSC Adv., 2016, 6: pp. 68504-68514.

(Continued)

Primary Examiner — Melissa S Mercier
(74) Attorney, Agent, or Firm — SALIWANCHIK, LLOYD & EISENSCHENK

(57) ABSTRACT

The present invention relates to compositions and methods for enhancing bioavailability of health-promoting substances, such as pharmaceuticals and nutritional supplements. The subject invention utilizes an adjuvant composition comprising one or more microbial-produced biosurfactants and/or isoforms thereof, to enhance bioavailability of health-promoting substances and to reduce the effective dosage that is required.

4 Claims, No Drawings

(56) References Cited

FOREIGN PATENT DOCUMENTS

| | | |
|---|---|---|
| JP | 4452799 B2 | 4/2010 |
| JP | 2011001314 A | 1/2011 |
| JP | 2014034552 A | 2/2014 |
| JP | 2014518878 A | 8/2014 |
| JP | 2016160244 A | 9/2016 |
| KR | 20150037774 A | 4/2015 |
| WO | 9107947 A1 | 6/1991 |
| WO | 9949876 A2 | 10/1999 |
| WO | WO-2011127101 A1 * 10/2011 | ............ A01N 25/30 |
| WO | 2011134998 A1 | 11/2011 |
| WO | WO-2013092421 A1 * 6/2013 | ............... C12N 9/18 |
| WO | WO-2014095367 A1 * 6/2014 | ............ A61K 8/463 |
| WO | 2014120247 A1 | 8/2014 |
| WO | 2015137357 A1 | 9/2015 |
| WO | 2016013026 A1 | 1/2016 |
| WO | 2016168197 A1 | 10/2016 |
| WO | 2017029175 A1 | 2/2017 |
| WO | 2017068349 A1 | 4/2017 |
| WO | 2017117049 A1 | 7/2017 |
| WO | 2018195296 A1 | 10/2018 |
| WO | 2019023039 A1 | 1/2019 |
| WO | 2019051380 A1 | 3/2019 |
| WO | 2019075456 A2 | 4/2019 |

OTHER PUBLICATIONS

De Almeida, D., et al., "Biosurfactants: Promising Molecules for Petroleum Biotechnology Advances." Frontiers in Microbiology, Oct. 2016, 7(1718): pp. 1-14.

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): pp. 161-174.

Gharaei-Fathabad, E., "Biosurfactants in Pharmaceutical Industry (A Mini-Review)." American Journal of Drug Discovery and Development, 2011, 1(1): pp. 58-69.

Irie, Y., et al., "Pseudomonas aeruginosa rhamnolipids disperse Bordetella bronchiseptica biofilms." FEMS Microbiology Letters, 2005, 250: pp. 237-243.

Joshi-Navare, K., et al., "A Biosurfactant-Sophorolipid Acts in Synergy with Antibiotics to Enhance Their Efficiency." BioMed Research International, 2013, vol. 2013, Article ID 512495, pp. 1-8.

Khafagy, E.-S., et al., "Rhamnolipids Enhance in Vivo Oral Bioavailability of Poorly Absorbed Molecules." Pharm Res, 2017, 34: pp. 2197-2210.

Kim, K., et al., "Characteristics of Sophorolipid as an Antimicrobial Agent." J. Microbiol. Biotechnol., 2002, 12(2): pp. 253-241.

Mao, J. C. H., et al., "Accumulation in gram-positive and gram-negative bacteria as a mechanism of resistance to erythromycin." Journal of bacteriology 95.3 (1968): pp. 1111-1117.

Mathew, D., et al., "Antiviral potential of curcumin." Journal of functional foods 40 (2018): pp. 692-699.

Nitschke, M., et al., "Production and properties of a surfactant obtained from Bacillus subtilis grown on cassava wastewater." Bioresource Technology, 2006, 97: pp. 336-341.

O'Brien, J. J., et al., "Acyclovir: an updated review of its antiviral activity, pharmacokinetic properties and therapeutic efficacy." Drugs 37 (1989): pp. 233-309.

Rivardo, F., et al., "Synergistic effect of lipopeptide biosurfactant with antibiotics against *Escherichia coli* CFT073 biofilm." International Journal of Antimicrobial Agents, 2011, 37: pp. 324-331.

Sen, R., "Biosurfactants: Advances in Experimental Medicine and Biology." Landes Bioscience and Springer Science +Business Media, LLC, 2010, 672: pp. 1-331.

Sharma, A et al., "A study on biosurfactant production in *Lactobacillus* and *Bacillus* sp." Int. J. Curr. Microbiol. App. Sci., 2014, 3(11): pp. 723-733.

Sil, J., et al., "Health Care Applications of Different Biosurfactants: Review." International Journal of Science and Research (IJSR), Oct. 2017, 6(10): pp. 41-50.

Specification Sheet, "Specification Sheet—Lactonic (Di-Acetylated) Sophorolipids." IB2MARKET Retrieved from the Internet: Aug. 19, 2021 <<./../../../media/17640/ib2market_specification-sheet_sophorolipids_june2015.pdf>>.

Ueno, Y., et al., "Characterization of Biosurfactant-Containing Liposomes and Their Efficiency for Gene Transfection." Biol. Pharm. Bull., Jan. 2007, 30(1): pp. 169-172.

Zhang, L., et al., "A natural lipopeptide of surfactin for oral delivery of insulin." Drug Delivery, 2016, 23(6): pp. 2084-2093.

Kulakovskaya, E. et al. "Physicochemical properties of yeast extracellular glycolipids." Extracellular Glycolipids of Yeasts; Academic Press: Cambridge, MA, USA (2014): 29-34.

Varvaresou, A., et al. "Biosurfactants in cosmetics and biopharmaceuticals." Letters in applied microbiology 61.3 (2015): 214-223.

\* cited by examiner

COMPOSITIONS FOR ENHANCING BIOAVAILABILITY OF PHARMACEUTICALS, SUPPLEMENTS AND INGESTED SUBSTANCES

CROSS-REFERENCE TO RELATED APPLICATIONS

This application is a continuation application of U.S. Patent Application No. 16/632,626, filed Jan. 21, 2020; which is a National Stage Application of International Application No. PCT/US2018/042885, filed Jul. 19, 2018; which claims priority to U.S. Provisional Patent Applications No. 62/537,502, filed Jul. 27, 2017, No. 62/647,974, filed Mar. 26, 2018, and No. 62/690,365, filed Jul. 27, 2018, all of which are incorporated by reference herein in their entirety.

BACKGROUND OF THE INVENTION

In general, bioavailability can refer to the rate and extent to which a substance reaches and enters a desired body system of a living organism, and can be effective therein. Specifically, bioavailability in the context of pharmacology is a measure of the rate and extent to which a drug reaches a site of action. In the realm of nutrition, bioavailability for food and dietary supplements can be defined as the proportion of an administered substance (or ingested substance) capable of being absorbed by the body and which is then available for use or storage in the body. Furthermore, bioavailability can also be the measure by which certain substances from the environment enter a living organism.

The bioavailability of a substance can play an important role in its usefulness for a living organism, and can change based on a variety of factors. For example, the bioavailability of ingested substances can be affected by the solubility of the substance, the rejection of the substance by the epithelium, or the speed at which the substance enters through the layers of the gastrointestinal (GI) tract. Substances with low solubility may not have a sufficient retention time, as they are incapable of penetrating either through the cells or the tight junctions between the cells of the GI tract. Thus, most, if not all of the substance is released from the body, unabsorbed and unused.

In addition to solubility, rejection of the substance is another factor affecting bioavailability. For example, many substances can be rejected by P-glycoprotein 1, a protein of the cell membrane that pumps foreign substances out of cells. More formally, it is an ATP-dependent efflux pump with broad substrate specificity. This pump is thought to have evolved as a defense mechanism against harmful substances, but can serve as an obstacle in many cases when a foreign, yet desirable, substance is sought to be introduced into the body. It is broadly distributed and expressed in the cells of a variety of organs, including the intestinal epithelium, where it pumps, for example, xenobiotics, back into the intestinal lumen; in liver cells, where it pumps substances into bile ducts; in the cells of the proximal tubule of the kidney, where it pumps substances into the urine-conducting ducts; and in the capillary endothelial cells composing the blood-brain barrier and blood-testis barrier, where it pumps substances back into the capillaries.

Pharmaceuticals, supplements and nutrition are important aspects of leading a healthy life; however, the dosage or amount of certain health-promoting substances that must be administered to a subject is often far greater than is actually needed to have a desired effect. This is because evolutionary obstacles hinder the bioavailability of certain compounds and nutrients from reaching a desired site of action, for example, through epithelial cells and through the blood-brain barrier.

Thus, there is a need for compositions and methods that are capable of enhancing the bioavailability of a broad range of pharmaceuticals, supplements, nutrients and other health-promoting substances that are administered to a subject.

BRIEF SUMMARY OF THE INVENTION

The subject invention provides materials and methods for improving the bioavailability of pharmaceuticals, supplements, nutrients and/or other health-promoting substances. In particular, the subject invention provides adjuvant compositions comprising microbial growth by-products for use in enhancing bioavailability of health-promoting substances. Advantageously, the microbe-based products and methods of the subject invention are non-toxic and cost-effective.

In certain specific embodiments, the subject invention provides approaches to enhancing bioavailability of a health-promoting substance using microbial growth by-products by, for example, suppressing P-glycoproteins and/or modulating other physical barrier mechanisms that would otherwise reduce the penetration of certain substances into, for example, a subject's epithelial cells and/or across the blood-brain barrier (BBB).

In one embodiment, adjuvant compositions are provided for enhancing bioavailability of a health-promoting compound, wherein said adjuvant compositions comprise therapeutically-effective amounts of one or more biosurfactants.

Biosurfactants are surface-active substances produced by microorganisms that lower the surface tension (or interfacial tension) between two liquids or between a liquid and a solid. All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces. Furthermore, biosurfactants accumulate at interfaces, and reduce the surface and interfacial tension between the molecules of liquids, solids, and gases, thus leading to the formation of aggregated micellular structures in solution.

Biosurfactants according to the subject invention include low molecular weight glycolipids (e.g., sophorolipids, rhamnolipids, mannosylerythritol lipids and trehalose lipids), lipopeptides (e.g., surfactin, iturin, fengycin and lichenysin), flavolipids, phospholipids, and high molecular weight polymers such as lipoproteins, lipopolysaccharide-protein complexes, and polysaccharide-protein-fatty acid complexes. In certain embodiments, the one or more biosurfactants are isolated and/or purified.

The one or more biosurfactants can further include any one or a combination of: a modified form, derivative, fraction, isoform or subtype of a biosurfactant, including forms that are naturally or artificially modified. The use of different isomers or forms of the biosurfactants is beneficial in that the skilled artisan can tailor the adjuvant composition depending upon its interactions with a particular health-promoting compound. That is, certain isoforms of a biosurfactant might be more effective with certain health-promoting compounds due to, for example, the chemical structure of the compound.

Preferably, the one or more biosurfactants are present in the subject adjuvant composition in critical micelle concentration (CMC).

In some embodiments, the adjuvant composition further comprises a therapeutically-effective dose of a target health-promoting compound, the bioavailability of which is sought to be enhanced. In this embodiment, the adjuvant composition can be mixed with the health-promoting compound. Alternatively, the adjuvant composition can be a separate composition from the target health-promoting compound, wherein the adjuvant composition is intended to be administered to a subject separately, but close in time to, the health-promoting compound.

The health-promoting compound can be, for example, a pharmaceutical compound, a nutritional supplement, or even simply water. In one embodiment, the subject compositions are formulated as an orally-consumable product, such as, for example, a capsule, a pill or a drinkable liquid. In another embodiment, the subject compositions are formulated to be administered via injection, suppository, inhalation, or any other mode of administration.

In one embodiment, the subject invention provides a delivery system for a health-promoting compound, wherein the biosurfactants of the adjuvant composition form a liposome or nanocapsule with the health-promoting compound encapsulated therein. In one embodiment, additional biological polymers can be included to provide further structure for the nanocapsule.

This nanocapsule delivery system can enhance the bioavailability of a health-promoting compound by protecting the compound from components in the blood, such as proteins and other molecules, that otherwise might bind to and/or degrade the compound and prevent it from arriving at a target site. The nanocapsule delivery system can allow for health-promoting compounds that might otherwise by degraded by acids or enzymes in the GI tract to be administered orally, as it creates a barrier against the acids or enzymes. In this regard, the delivery system can comprise an enteric coating. Furthermore, the nanocapsule delivery system formulation allows for time release of the health-promoting compound, thereby reducing the potential toxicity or potential negative side-effects of a compound in a subject.

The subject invention further provides a method of enhancing the bioavailability of a health-promoting compound, which comprises administering a therapeutically-effective amount of an adjuvant composition of the subject invention to a subject in need thereof and administering a therapeutically-effective amount of the health-promoting compound to the subject.

The methods can further be used to allow for oral administration of health-promoting compounds that might otherwise by degraded by acids or enzymes in the GI tract. Furthermore, the methods can be used to reduce the dosage required for a health-promoting compound, and reduce the potential toxicity or potential negative side-effects of a compound in a subject.

In preferred embodiments, the adjuvant composition comprises one or more biosurfactants, including any modified form, derivative, fraction, isoform or subtype of biosurfactants selected from, for example, a sophorolipid, rhamnolipid, mannosylerythritol lipid, trehalose lipid, surfactin, iturin, fengycin and lichenysin. The health-promoting compound can be administered simultaneously with the adjuvant composition or otherwise close in time to administering the adjuvant composition.

Health-promoting compounds (or health-promoting substances) comprise any molecule or molecules that are meant to be delivered into blood and/or lymphatic circulation, as well as into tissues and organs, and ultimately reach a site in a subject's body where a positive impact on the subject's health can be effected. Non-limiting examples of health-promoting compounds include pharmaceuticals and/or nutritional supplements categorized as pain-relievers, antihistamines, antivirals, anticancer and/or chemotherapeutic compounds, antibiotics, antimicrobials, antiseizure compounds, anti-inflammatory compounds, vaccines, cholesterol-lowering compounds, antidepressants, vitamins, minerals, nutrients, water and many others.

In one embodiment, the health-promoting substance is an orally deliverable health-promoting substance, which, in particular, is any molecule or molecules that is delivered via initial absorption into the gastrointestinal tract or into the mucus membranes of the mouth (e.g., by way of sublingual or buccal administration).

Advantageously, the materials and methods of the subject invention can help improve the quality of life for individuals who are either suffering from a particular health condition or who are already healthy (e.g., generally free from illness or injury) but are simply seeking to enhance their state of being. Furthermore, the subject invention can be used to reduce the dosage of certain pharmaceuticals and/or supplements that are required to be considered therapeutically-effective, thus reducing the cost and potential toxicity and/or negative side-effects that might arise from administering them to a subject.

DETAILED DESCRIPTION

The subject invention provides materials and methods for improving the bioavailability of pharmaceuticals, supplements, nutrients and/or other health-promoting substances. In particular, the subject invention provides adjuvant compositions comprising microbial growth by-products for use in enhancing bioavailability of health-promoting substances. Advantageously, the microbe-based products and methods of the subject invention are non-toxic and cost-effective.

Further described herein are approaches to enhancing bioavailability of a health-promoting compound, which utilize microbial growth by-products to, for example, suppress P-glycoproteins and modulate other blood plasma proteins and/or physical barrier mechanisms that reduce the penetration of certain compounds into a subject's epithelial cells and/or across the BBB. The subject invention also provides methods for reducing the dosage of a health-promoting compound required for the health-promoting compound to be therapeutically-effective in a subject.

Selected Definitions

As used herein, the term "adjuvant" in the context of the subject compositions means an auxiliary compound that can aid in, contribute to, and/or enhance the effectiveness of a substance that is administered with the adjuvant. For example, an adjuvant can be taken alongside or included in a prescription drug or a supplement to aid in the effectiveness of the active, primary active ingredient(s), whatever the purpose may be (e.g., treating a disease or enhancing the functioning of an organ or system in the body).

As used herein, the term "subject" refers to an animal, such as a mammal, needing or desiring delivery of the benefits provided by a health-promoting substance. The animal may be for example, pigs, horses, goats, cats, mice, rats, dogs, apes, fish, chimpanzees, orangutans, guinea pigs, hamsters, cows, sheep, birds, e.g., chickens, as well as any other vertebrate or invertebrate. These benefits can include, but are not limited to, treatment of a health condition, disease or disorder; prevention of a health condition, disease or disorder; hydration or rehydration; nutritional enhancement and/or supplementation for, e.g., athletic performance or weight control; immune health; enhancement of function of an organ, tissue or system in the body; and/or simply pleasure. The preferred subject in the context of this invention is a human, either male or female. In some embodiments, a subject is suffering from a health condition, disease or disorder, while in some embodiments, the subject is in a state of good health (i.e., free from injury or illness), but desires enhanced health and/or functioning of an particular organ, tissue or body system. The subject can be of any age or stage of development, including infant, toddler, adolescent, teenager, adult, and senior.

As used herein, the terms "therapeutically-effective amount," "therapeutically-effective dose," "effective amount," and "effective dose" are used to refer to an amount or dose of a compound or composition that, when administered to a subject, is capable of treating or improving a condition, disease or disorder in a subject, or that is capable of providing enhancement in health or function to an organ, tissue or body system. In other words, when administered to a subject, the amount is "therapeutically effective." The actual amount will vary depending on a number of factors including, but not limited to, the particular condition, disease or disorder being treated or improved; the severity of the condition; the particular organ, tissue or body system of which enhancement in health or function is desired; the size, age, and health of the patient; and the route of administration.

As used herein, the term "treatment" refers to eradicating, reducing, ameliorating, or reversing a sign or symptom of a health condition, disease or disorder to any extent, and includes, but does not require, a complete cure of the condition, disease or disorder. Treating can be curing, improving, or partially ameliorating a disorder. "Treatment" can also include improving or enhancing a condition or characteristic, for example, bringing the function of a particular system in the body to a heightened state of health or homeostasis.

As used herein, "preventing" a health condition, disease or disorder refers to avoiding, delaying, forestalling, or minimizing the onset of a particular sign or symptom of the condition, disease or disorder. Prevention can, but is not required to be, absolute or complete, meaning the sign or symptom may still develop at a later time. Prevention can include reducing the severity of the onset of such a condition, disease or disorder, and/or inhibiting the progression of the condition, disease or disorder to a more severe condition or disorder.

As used herein, reference to a "microbe-based composition" means a composition that comprises components that were produced as the result of the growth of microorganisms or other cell cultures. A microbe-based composition may comprise the microbes themselves, or the microbes may be separated from the broth in which they were cultivated, and the composition comprises residual cellular components and/or by-products of microbial growth. Preferably, the compositions according to the subject invention have been separated from the microbes. The by-products of microbial growth may be, for example, metabolites (e.g., biosurfactants), cell membrane components, expressed proteins, and/or other cellular components.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers and/or appropriate carriers (e.g., water or salt solutions). The microbe-based product may comprise mixtures of microbe-based compositions. The microbe-based product may also comprise one or more components of a microbe-based composition that have been processed in some way such as, but not limited to, filtering, centrifugation, lysing, drying, purification and the like.

As used herein, "harvested" refers to removing some or all of the microbe-based composition from a growth vessel.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

A "metabolite" refers to any substance produced by metabolism (i.e., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, biosurfactants, enzymes, acids, solvents, gasses, alcohols, proteins, vitamins, minerals, microelements, amino acids, and polymers.

By "modulate" is meant alter (increase or decrease). Such alterations are detected by standard art known methods such as those described herein.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, or 20 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 1%, 5%, 10%, 25%, 50%, 75%, or 100%.

By "reference" is meant a standard or control condition.

As used herein, a "biofilm" is a complex aggregate of microorganisms, such as bacteria, wherein the cells adhere to each other. The cells in biofilms are physiologically distinct from planktonic cells of the same organism, which are single cells that can float or swim in liquid medium.

As used herein, "surfactant" refers to a surface-active substance that lowers the surface tension (or interfacial tension) between two liquids or between a liquid and a solid. Surfactants act as, for example, detergents, wetting agents, emulsifiers, foaming agents, and/or dispersants. A surface-active substance produced by microorganisms is referred to as a "biosurfactant."

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention, e.g., the ability to improve the bioavailability of a substance.

Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Formulation and Delivery of Adjuvant Composition

The subject invention provides adjuvant compositions comprising microbial growth by-products for use in enhancing bioavailability of pharmaceuticals, supplements, nutrients and other health-promoting substances. Advantageously, the microbe-based products and methods of the subject invention are non-toxic and cost-effective.

In one embodiment, adjuvant compositions are provided for enhancing bioavailability of a health-promoting compound, wherein said adjuvant compositions comprise therapeutically-effective amounts of one or more biosurfactants.

In some embodiments, the adjuvant composition further comprises a therapeutically-effective dose of a health-promoting compound, the bioavailability of which is sought to be enhanced. In this embodiment, the adjuvant and the health-promoting compound are included together as one formulation with other optional additives.

Alternatively, the adjuvant composition can be administered to a subject separately from, but close in time to (e.g., five minutes or less before or after), administration of a target health-promoting compound.

Advantageously, the adjuvant composition of the subject invention is capable of reducing a liquid's surface tension and reducing the interfacial tension between liquid-liquid and liquid-solid interfaces. Additionally, a target health-promoting compound can exhibit resistance to degradation by digestive juices (e.g., acids and enzymes) when administered into the gastrointestinal (GI) system along with the subject adjuvant composition. Furthermore, in certain embodiments, the subject adjuvant composition can help suppress and/or modulate the activity of, for example, blood plasma proteins, P-glycoproteins, and other barriers and cell junctions that prevent certain compounds from penetrating into a target site of the body.

The adjuvant composition preferably comprises biosurfactants, which are surface-active substances produced by microorganisms. The biosurfactants useful according to the subject invention are safe, biodegradable and can be produced with ease at low cost using selected organisms in or on renewable substrates.

All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces. Furthermore, biosurfactants accumulate at interfaces, and reduce the surface and interfacial tension between the molecules of liquids, solids, and gases, thus leading to the formation of aggregated micellular structures in solution.

Most biosurfactant-producing organisms produce biosurfactants in response to the presence of a hydrocarbon source (e.g., oils, sugar, glycerol, etc.) in the growing media. Other media components such as concentration of iron can also affect biosurfactant production significantly. Microbial biosurfactants are produced by a variety of microorganisms such as bacteria, fungi, and yeasts, such as, for example, *Pseudomonas* spp. (*P. aeruginosa, P. putida, P. florescens, P. fragi, P. syringae*); *Flavobacterium* spp.; *Bacillus* spp. (*B. subtilis, B. pumillus, B. cereus, B. licheniformis*); *Wickerhamomyces* spp. (*W. anomalus*), *Candida* spp. (*C. albicans, C. rugosa, C. tropicalis, C. lipolytica, C. torulopsis*); *Rhodococcus* spp.; *Arthrobacter* spp.; *Campylobacter* spp.; *Cornybacterium* spp.; *Pichia* spp. (*P. anomala, P. occidentalis*); *Starmerella* spp. (*S. bombicola*); and so on.

The biosurfactants may be obtained by fermentation processes known in the art, e.g., solid-state fermentation, submerged fermentation, or combinations thereof. The biosurfactant produced by microorganisms of interest may be retained in the microorganisms or secreted into their growth medium. The growth medium may contain compounds that stabilize the activity of the biosurfactant. Furthermore, the growth by-product may be isolated, concentrated and/or purified.

Biosurfactants according to the subject invention include low molecular weight glycolipids (e.g., sophorolipids, rhamnolipids, mannosylerythritol lipids and trehalose lipids), lipopeptides (e.g., surfactin, iturin, fengycin and lichenysin), flavolipids, phospholipids, and high molecular weight polymers such as lipoproteins, lipopolysaccharide-protein complexes, and polysaccharide-protein-fatty acid complexes.

The one or more biosurfactants can further include one or a combination of: a modified form, derivative, fraction, isoform or subtype of a biosurfactant, including forms that are naturally or artificially modified. The use of different isomers or forms of biosurfactants is beneficial in that the skilled artisan can tailor the adjuvant composition depending upon its interactions with a particular health-promoting compound. That is, certain isoforms of a biosurfactant might be more effective with certain health-promoting compounds due to, for example, the chemical structure of the compound.

In certain embodiments, the biosurfactant is a sophorolipid (SLP), such as, for example, a lactonic or acidic form sophorolipid, a non-acetylated sophorolipid, a mono-acetylated sophorolipid, a di-acetylated sophorolipid, or any other isoform thereof.

In certain embodiments, the biosurfactant is a rhamnolipid (RLP), such as, for example, a mono-rhamnolipid, a di-rhamnolipid, or any other isoform thereof.

In certain embodiments, the biosurfactant is a mannosylerythritol lipid (MEL), such as, for example, MEL-A, MEL-B, MEL-C, or MEL-D, or any other isoforms with varying fatty acid lengths and/or hydrophobic portions.

In certain embodiments, the biosurfactant is a trehalose lipid (TL) or any other isoform thereof.

In certain embodiments, the biosurfactant is a lipopeptide, including linear or cyclic form lipopeptides, or any other isoforms thereof. As an example, surfactin is a lipopeptide that can have a structure comprising a peptide loop of seven amino acids and a hydrophobic fatty acid chain thirteen to fifteen carbons long. In an exemplary embodiment, the amino acids comprise L-aspartic acid, L-leucine, glutamic acid, L-leucine, L-valine and two D-leucines.

As another example, iturin is a lipopeptide with a structure comprising a peptide loop of seven amino acids and a β-amino fatty acid chain that can vary from 14 to 17 carbons long. In one embodiment, iturin A is utilized according to the subject invention.

The biosurfactants are preferably present in the adjuvant composition in therapeutically-effective amounts. In one embodiment, this means the biosurfactants are present in critical micelle concentration (CMC). CMC is the concentration of surfactants above which micelles will form and all additional surfactants added to the system either convert to micelles or add to the existing micelles.

In certain embodiments, a therapeutically-effective amount of biosurfactants in the composition is 0.001 to 90% by weight (wt %), preferably 50 wt % or less, more preferably 25 wt % or less, even more preferably 10 wt % or less. In certain embodiments, the biosurfactant is present at more than 0.01, 0.02, 0.03, 0.05, 0.08, 0.1, 0.2, or 0.5%.

In some embodiments, the adjuvant composition further comprises a therapeutically-effective dose of a target health-promoting compound, the bioavailability of which is sought to be enhanced. In this embodiment, the adjuvant composition can be mixed with the health-promoting compound. Alternatively, the adjuvant composition can be a separate composition from the target health-promoting compound, wherein the adjuvant composition is intended to be administered to a subject at the same time as the health-promoting compound.

The health-promoting compound can be, for example, a pharmaceutical compound, a nutritional supplement, or even simply water. In one embodiment, the subject compositions are formulated as an orally-consumable product, such as, for example, a capsule, a pill or a drinkable liquid. In another embodiment, the subject compositions are formulated to be administered via injection, inhalation, or any other mode of administration.

The subject invention is useful for enhancing the bioavailability of "health-promoting compounds" or "health-promoting substances," which comprise any molecule or molecules that are meant to be delivered into blood and/or lymphatic circulation, as well as into tissues and organs, and ultimately reach a site in a subject's body where a positive impact on the subject's health, either locally or systemically, can be effected. Health-promoting compounds include, for example, any category of supplement and/or pharmaceutical (including biopharmaceuticals) used for, for example, relieving pain, fever and/or inflammation; reducing the symptoms of allergies or colds; suppressing or treating a virus; treating cancer; treating a microbial infection; suppressing or preventing seizures; lowering or managing cholesterol; managing diabetes; treating depression or anxiety; hydrating or rehydrating; controlling body weight; enhancing athletic performance; and reducing or enhancing fertility, to name just a few.

In one embodiment, the adjuvant composition is formulated as a delivery system for a health-promoting compound, wherein the biosurfactants of the adjuvant composition form a liposome or nanocapsule with the health-promoting compound encapsulated therein. In one embodiment, additional biological polymers can be included to provide further structure for the nanocapsule.

This nanocapsule delivery system can enhance the bioavailability of a health-promoting compound by protecting the compound from components in the blood, such as proteins and other molecules, that otherwise might bind to the compound and prevent it from penetrating a target site. Additionally, the nanocapsule delivery system can allow for health-promoting compounds that might otherwise by degraded by acids or enzymes in the GI tract to be administered orally, as it creates a barrier against the acids or enzymes. Furthermore, the nanocapsule delivery system formulation allows for time release of the health-promoting compound, thereby reducing the potential toxicity or potential negative side-effects of a compound in a subject.

In one embodiment, the adjuvant composition can be formulated to comprise an orally deliverable health-promoting substance and/or to be administered simultaneously with one as an orally consumable product. An orally deliverable health-promoting substance is any physiologically active substance delivered via initial absorption into the gastrointestinal tract, or into the mucus membranes of the mouth (e.g., by way of sublingual or buccal administration).

Orally consumable products according to the invention are any preparations or compositions suitable for consumption, for nutrition, for oral hygiene or for pleasure, and are products intended to be introduced into the human or animal oral cavity, to remain there for a certain period of time and then to either be swallowed (e.g., food ready for consumption or pills) or to be removed from the oral cavity again (e.g., chewing gums or products of oral hygiene or medical mouth washes). While an orally-deliverable health-promoting substance can be formulated into an orally consumable product, and an orally consumable product can comprise an orally-deliverable health-promoting substance, the two terms are not meant to be used interchangeably herein.

Orally consumable products include all substances or products intended to be ingested by humans or animals in a processed, semi-processed or unprocessed state. This also includes substances that are added to orally-consumable products (particularly food and pharmaceutical products) during their production, treatment or processing and intended to be introduced into the human or animal oral cavity.

Orally-consumable products can also include substances intended to be swallowed by humans or animals and then digested in an unmodified, prepared or processed state; the orally consumable products according to the invention therefore also include casings, coatings or other encapsulations that are intended also to be swallowed together with the product or for which swallowing is to be anticipated.

In one embodiment, the orally-consumable product is a capsule, pill, syrup, emulsion or liquid suspension containing a desired orally-deliverable substance. In one embodiment, the orally-consumable product can comprise an orally-deliverable substance in powder form, which can be mixed with water or another liquid to produce a drinkable orally-consumable product.

In some embodiments, the orally-consumable product according to the invention can comprise one or more formulations intended for nutrition or pleasure. These particularly include baking products (e.g., bread, dry biscuits, cake, and other pastries), sweets (e.g., chocolates, chocolate bar products, other bar products, fruit gum, coated tablets, hard caramels, toffees and caramels, and chewing gum), alcoholic or non-alcoholic beverages (e.g., cocoa, coffee, green tea, black tea, black or green tea beverages enriched with extracts of green or black tea, Rooibos tea, other herbal teas, fruit-containing lemonades, isotonic beverages, soft drinks, nectars, fruit and vegetable juices, and fruit or vegetable juice preparations), instant beverages (e.g., instant cocoa beverages, instant tea beverages, and instant coffee beverages), meat products (e.g., ham, fresh sausage preparations or raw sausage preparations, and seasoned oder, marinated fresh meat or salted meat products), eggs or egg products (e.g., dried whole egg, egg white, and egg yolk), cereal products (e.g., breakfast cereals, muesli bars, and pre-cooked instant rice products), dairy products (e.g., whole fat or fat reduced or fat-free milk beverages, rice pudding, yoghurt, kefir, cream cheese, soft cheese, hard cheese, dried milk powder, whey, butter, buttermilk, and partly or wholly hydrolyzed products containing milk proteins), products from soy protein or other soy bean fractions (e.g., soy milk and products prepared thereof, beverages containing isolated or enzymatically treated soy protein, soy flour containing beverages, preparations containing soy lecithin, fermented products such as tofu or tempeh products prepared thereof and mixtures with fruit preparations and, optionally, flavoring substances), fruit preparations (e.g., jams, fruit ice cream, fruit sauces, and fruit fillings), vegetable preparations (e.g., ketchup, sauces, dried vegetables, deep-freeze vegetables, pre-cooked vegetables, and boiled vegetables), snack articles (e.g., baked or fried potato chips (crisps) or potato dough products, and extrudates on the basis of maize or peanuts), products on the basis of fat and oil or emulsions thereof (e.g., mayonnaise, remoulade, and dressings), other ready-made meals and soups (e.g., dry soups, instant soups, and pre-cooked soups), seasonings (e.g., sprinkle-on seasonings), sweetener compositions (e.g., tablets, sachets, and other preparations for sweetening or whitening beverages or other food). The present compositions may also serve as semi-finished products for the production of other compositions intended for nutrition or pleasure.

In one embodiment, the adjuvant composition can be formulated to comprise a health-promoting substance and/or to be administered simultaneously with one via a route of administration, including, for example, injection (e.g., intravenous (IV), intramuscular (IM), intraperitoneal, intrathecal or subcutaneous), transdermal, rectal, urogenital (e.g., vaginal), ocular, aural, nasal, inhalation and cutaneous routes.

The subject composition can further comprise one or more pharmaceutically acceptable carriers and/or excipients, and can be formulated into preparations in, for example, solid, semi-solid, liquid or gaseous forms, such as tablets, capsules, powders, granules, ointments, gels, lotions, solutions, suppositories, drops, patches, injections, inhalants and aerosols.

The term "pharmaceutically acceptable" as used herein means compatible with the other ingredients of a pharmaceutical composition and not deleterious to the recipient thereof.

Carriers and/or excipients according the subject invention can include any and all solvents, diluents, buffers (such as, e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilisers (such as, e.g., Tween 80, Polysorbate 80), colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavorings, aromatisers, thickeners, coatings, preservatives (such as, e.g., Thimerosal, benzyl alcohol), antioxidants (such as, e.g., ascorbic acid, sodium metabisulfite), tonicity controlling agents, absorption delaying agents, adjuvants, bulking agents (such as, e.g., lactose, mannitol) and the like. The use of carriers and/or excipients in the field of drugs and supplements is well known. Except for any conventional media or agent that is incompatible with the target health-promoting substance or with the adjuvant composition, its use in the subject compositions may be contemplated.

In one embodiment, the adjuvant composition can be made into aerosol formulations so that, for example, it can be nebulized or inhaled. Suitable pharmaceutical formulations for administration in the form of aerosols or sprays are, for example, solutions, suspensions or emulsions. Formulations for oral or nasal aerosol or inhalation administration may also be formulated with illustrative carriers, including, for example, saline, polyethylene glycol or glycols, DPPC, methylcellulose, or in mixture with powdered dispersing agents or fluorocarbons. Aerosol formulations can be placed into pressurized propellants, such as dichlorodifluoromethane, propane, nitrogen, fluorocarbons, and/or other solubilizing or dispersing agents known in the art. Illustratively, delivery may be by use of a single-use delivery device, a mist nebulizer, a breath-activated powder inhaler, an aerosol metered-dose inhaler (MDI) or any other of the numerous nebulizer delivery devices available in the art. Additionally, mist tents or direct administration through endotracheal tubes may also be used.

In one embodiment, the adjuvant composition can be formulated for administration via injection, for example, as a solution or suspension. The solution or suspension can comprise suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Further components can be added to the compositions as are determined by the skilled artisan such as, for example, buffers, carriers, viscosity modifiers, preservatives, flavorings, dyes and other ingredients specific for an intended use. One skilled in this art will recognize that the above description is illustrative rather than exhaustive. Indeed, many additional formulations techniques and pharmaceutically-acceptable excipients and carrier solutions suitable for particular modes of administration are well-known to those skilled in the art.

Methods of Enhancing Bioavailability of Health-Promoting Substances

The subject invention further provides methods of enhancing the bioavailability of a health-promoting substance in a subject in need thereof, which comprises administering a therapeutically-effective amount of an adjuvant composition comprising one or more biosurfactants to the subject and administering a therapeutically-effective amount of the health-promoting compound to the subject.

The method can also be used to reduce the dosage required for a health-promoting compound, and reduce the potential toxicity or potential negative side-effects of a compound in a subject. Furthermore, the method can be used to allow for oral administration of health-promoting compounds that might otherwise by degraded by acids or enzymes in the GI tract The health-promoting compound can be administered simultaneously with the adjuvant composition, for example, as part of a single formulation. In one embodiment, the method comprises administering the health-promoting compound to the subject using the adjuvant nanocapsule delivery system described herein.

Alternatively, the health-promoting compound can be administered separately from the adjuvant composition. In this alternate embodiment, the health-promoting compound is administered either immediately before or immediately after the adjuvant composition is administered, wherein "immediately before" or "immediately after" means 5 minutes, 4 minutes, 3 minutes, 2 minutes, 1 minute, 30 seconds or less before or after.

In preferred embodiments, the biosurfactants of the adjuvant composition are selected from, for example, glycolipids (e.g., SLP, RLP, MEL and TL), lipopeptides (e.g., surfactin, iturin, fengycin and lichenysin), and any modified form, derivative, fraction, isoform or subtype thereof. Combinations of biosurfactants and their various forms are also envisioned.

As used herein, "administering" a composition or product refers to delivering it to a subject such that it contacts a target or site such that the composition or product can have an effect on that target or site. The effect can be due to, for example, the action of a health-promoting compound, or due to a biosurfactant composition. Administration can be acute or chronic (e.g., daily, weekly, monthly, etc.) or in combination with other agents. The subject adjuvant composition, whether administered in the same formulation as the target health-promoting compound or within, for example, 5 minutes of the target compound, can be administered by any route of administration provided it is formulated for such a route. In this way, the therapeutic effects attainable by the methods and compositions of the invention can be, for example, systemic, local, tissue-specific, etc., depending of the specific needs of a given application of the invention.

In one embodiment, compositions according to the subject invention can be ingested by a subject in order for the compositions to be contacted with the gastrointestinal tract (e.g., the target site) and have a desired local effect therein or to be absorbed therein for systemic effects. Administration can also be achieved through, for example, injection (e.g., intravenous (IV), intramuscular (IM), intraperitoneal, intrathecal or subcutaneous), transdermal, rectal, urogenital (e.g., vaginal), ocular, aural, nasal, mucosal, inhalation and cutaneous routes.

In one embodiment, the health-promoting compound is a supplement. The supplement can be synthetic, or can be naturally-derived, for example, originating from microbial, fungal, plant or animal sources. The supplement can be a dietary and/or nutritional supplement, for example, providing nutrients such as vitamins (e.g., A (retinoids), B1 (thiamine), B2 (riboflavin), B3 (niacin), B5 (panthothenic acid), B6 (pyridoxine), B9 (folic acid), B12 (cobalamin), C (ascorbic acid), D (calciferol), E (tocopherol), H (biotin), K, and/or derivatives thereof); electrolytes and minerals (e.g., calcium, phosphorous, magnesium, potassium, sodium chloride, iodine, zinc, iron, copper, chromium, fluoride, selenium, manganese, and molybdenum); and fats, carbohydrates and/or proteins (e.g., whey, hemp, soy, collagen, amino acids). The supplement can be a source of energy, alertness, and/or increased physical performance, providing, for example, caffeine, yerba mate, creatine and/or guarana. The supplement can also be a botanical or herbal supplement, for example, turmeric root or ginseng, for holistic health benefits.

In one embodiment, the health-promoting compound is water, wherein the adjuvant composition can be administered as an enhanced hydration or rehydration compound to increase the bioavailability and absorption of water in the GI tract.

In one embodiment, the health-promoting compound is a pharmaceutical or biopharmaceutical. As used herein, the phrase "pharmaceutical" refers to a compound manufactured for use as a medicinal and/or therapeutic drug, whether prescribed by a health care professional or available over the counter. As used herein, the phrase "biopharmaceutical" refers to a biological macromolecule or cellular component, such as a blood product, used as a pharmaceutical. Biopharmaceuticals are typically manufactured in, extracted from, or semi-synthesized from biological sources.

In one embodiment, the pharmaceutical is selected from an antiviral (e.g., acyclovir or valacyclovir), an antibiotic (e.g., erythromycin), and a pain-reliever and/or anti-inflammatory compound (e.g., ibuprofen or aspirin).

Additional, and non-limiting examples of pharmaceuticals that can be health-promoting compounds according to the subject invention include, analgesics (e.g., NSAIDs, opioids, acetaminophen, naproxen and local anesthetics); muscle relaxants; digestive aids (e.g., antacids, reflux suppressants, PPIs, laxatives, probiotics, prebiotics, and antidiarrheals); cardiovascular drugs (e.g., beta blockers, calcium channel blockers, diuretics, vasoconstrictors, vasodilators, cardiac glycosides, antiarrhythmics, nitrates); blood pressure/hypertension drugs (e.g., ACE inhibitors, alpha blockers, angiotensin receptor blockers); coagulation drugs (e.g., anticoagulants, heparin, antiplatelet drugs, fibrinolytics, anti-hemophilic factors and haemostatic drugs); statins (e.g., LDL cholesterol inhibitors and hypolipidaemic agents); endocrine aids (e.g., androgens, antiandrogens, estrogens, gonadotropin, corticosteroids, HGH, vasopressin); antidiabetics (e.g., sulfonylureas, biguanides, metformin, thiazolidinediones, insulin); thyroid hormones and antithyroid drugs; urogenital system drugs (e.g., antifungals, alkalinizing agents, quinolones, antibiotics, cholinergics, anticholinergics, fertility medications, hormonal contraceptives); central nervous system drugs (e.g., psychedelics, hypnotics, anesthetics, antipsychotics, eugeroics, antidepressants (including tricyclics, monoamine oxidase inhibitors, lithium salts, and SSRIs), antiemetics, anticonvulsants/antiepileptics, stimulants, amphetamines, dopamine agonists, antihistamines, cannabinoids, 5-HT antagonists); ocular medications (e.g., topical anesthetics, sympathomimetics, parasympatholytics, mydriatics, cycloplegics, mast cell inhibitors); antimicrobials (e.g., antibiotics, antibacterials, antifungals, antiparasitics, antiprotozoals, amoebicides); antivirals (e.g., acyclovir, ribavirin, valacyclovir, famciclovir), antihistamines, anticholinergics, antiseptics, cerumenolytics, bronchodilators, antitussives, mucolytics, decongestants, antimalarials, antitoxins, antivenoms, vaccines, immunoglobulins, immunosuppressants, interferons, monoclonal antibodies, chemotherapeutic drugs and/or any other category of compounds that are capable of treating any health condition, disease or disorder, or of enhancing health in any way.

What is claimed:

1. A method for administering a health-promoting substance to a tissue in a subject, the method comprising administering, to the subject, an effective amount of a composition comprising a purified sophorolipid, a purified mannosylerythritol lipid (MEL), and said health-promoting substance; wherein said health-promoting substance is an antibiotic or an anti-inflammatory substance; and wherein said composition is administered to the subject via transdermal or cutaneous administration; and wherein the health-promoting substance is encapsulated in a nanocapsule formed by the sophorolipid and the MEL.

2. The method of claim 1, wherein the composition further comprises a pharmaceutically-acceptable carrier.

3. The method of claim 1, wherein the sophorolipid, the MEL, or both the sophorolipid and the MEL, are present in the composition in critical micelle concentration (CMC).

4. The method of claim 1, wherein at least 60% by weight of said purified sophorolipid is in an acidic form.

* * * * *